United States Patent
Desaphy et al.

(10) Patent No.: US 11,707,441 B2
(45) Date of Patent: Jul. 25, 2023

(54) SAFINAMIDE FOR TREATING MYOTONIA

(71) Applicant: Zambon S.P.A., Bresso (IT)

(72) Inventors: Jean-François Desaphy, Cellamare (IT); Sabata Pierno, Cellamare (IT); Diana Conte, Bari (IT); Elsa Melloni, Milan (IT); Silvia Vailati, Arcore (IT); Gloria Padoani, Locate Triulzi (IT); Carla Caccia, Gallarate (IT)

(73) Assignee: Zambon S.P.A., Bresso (IT)

( * ) Notice: Subject to any disclaimer, the term of this patent is extended or adjusted under 35 U.S.C. 154(b) by 61 days.

(21) Appl. No.: 17/058,785

(22) PCT Filed: May 28, 2019

(86) PCT No.: PCT/EP2019/063733
§ 371 (c)(1),
(2) Date: Nov. 25, 2020

(87) PCT Pub. No.: WO2019/229028
PCT Pub. Date: Dec. 5, 2019

(65) Prior Publication Data
US 2021/0196657 A1    Jul. 1, 2021

(30) Foreign Application Priority Data
May 29, 2018   (EP) .................... 18000481

(51) Int. Cl.
*A61K 31/165* (2006.01)
*A61P 21/00* (2006.01)

(52) U.S. Cl.
CPC ............ *A61K 31/165* (2013.01); *A61P 21/00* (2018.01)

(58) Field of Classification Search
CPC ............................. A61K 31/165; A61P 21/00
See application file for complete search history.

(56) References Cited

U.S. PATENT DOCUMENTS

| | | | | |
|---|---|---|---|---|
| 2011/0172190 A1* | 7/2011 | Marks | ............... | C07D 281/10 514/211.09 |
| 2012/0329800 A1* | 12/2012 | Bonaldo | ............. | A61K 31/421 514/354 |
| 2014/0051709 A1* | 2/2014 | Reddy | ............... | C07D 413/04 549/287 |

OTHER PUBLICATIONS

Logigian et al. (Neurology (2010) 1441-1448,). (Year: 2010).*
Cattaneo C. et al., "Long-term efficacy of safinamide on Parkinson's Disease chronic pain", Advances in Therapy, Health Communications, Metuchen, NJ, US, vol. 35, No. 4, Mar. 14, 2018, pp. 515-522.
Cattaneo C. et al., Safinamide as add-on therapy to levodopa in mid- to late-stage Parkinson's Disease fluctuating patients: post-hoc analysis of studies 016 and settle:, Journal of Parkinson's Disease, vol. 6, No. 1, Mar. 30, 2016, pp. 165-173.
Eijkelkamp N. et al., "Neurological perspective on voltage-gated sodium channels", Brain, vol. 135, No. 9, Sep. 1, 2012, pp. 2585-2612.
Logician E.L. et al., "Mexilene is an effective antimyotonia treatment in myotonic dystrophy type 1", Neurology, May 4, 2010, pp. 1441-1448.
Search Report and Written Opinion of PCT/EP2019/063733 dated Aug. 2, 2019.
Vitiello L., et al., "Drug repurposing for Duchenne Muscular Dystrophy: the monoamine oxidase B inhibitor safinamide ameliorates the pathological phenotype in mdx mice and myogenic cultures from DMD patients", Frontiers in Physiology, vol. 9, Aug. 14, 2018.

* cited by examiner

*Primary Examiner* — Marcos L Sznaidman
(74) *Attorney, Agent, or Firm* — Silvia Salvadori, P.C.; Silvia Salvadori

(57) ABSTRACT

The present invention relates to safinamide or a pharmaceutically acceptable salt thereof for use in the treatment of a condition caused by pathological sarcolemma hyperexcitability, and/or of any other condition in which the restoration of normal sarcolemma excitability may produce a therapeutic benefit or improvement, wherein said condition is preferably a myotonic disorder.

15 Claims, 2 Drawing Sheets

SAFINAMIDE FOR TREATING MYOTONIA

This application is a U.S. national stage of PCT/EP2019/063733 filed on 28 May 2019, which claims priority to and the benefit of European Patent Application No. 18000481.4, filed on 29 May 2018, the contents of which are incorporated herein by reference in their entireties.

TECHNICAL FIELD

The present invention relates to safinamide or a pharmaceutically acceptable salt thereof for use in the treatment of myotonia. In particular, the present invention relates to pharmaceutical compositions comprising safinamide or pharmaceutically acceptable salt thereof for use in the treatment of a disease or condition, wherein myotonia is an undesired aspect.

BACKGROUND OF THE INVENTION

Myotonia can be defined as an involuntary persistence of skeletal muscles contraction after activation, which causes stiffness and pain.

Myotonia stems from an abnormality of the muscle fiber membrane (pathological sarcolemma hyperexcitability) that results in an extended delay before muscles can relax after a contraction and can be painful and badly interfere with daily motor activities and quality of life. A muscle starts its contraction on cue, but the electrical activity continues after the nerve signal has ended, causing a stiffness or "locking up" of the muscle.

The debilitating slowed muscle relaxation experienced by patients with myotonic disorders is caused by involuntary firing of action potentials (APs). In physiological conditions, chloride currents (mediated by the chloride channel ClC-1) which account for 70 to 80% of resting muscle membrane conductance, offset the depolarizing influence of K+ accumulation in muscle T-tubules (Adrian and Bryant, J Physiol 1974; 240:505-515) and prevent the voltage-gated Na+ channel opening thus avoiding the involuntary APs and repetitive discharge observed in myotonia.

Mutations in genes coding for skeletal muscle chloride (CLCN1) and/or sodium channels (SCN4A) result in multiple defects in channel gating leading to muscle hyperexcitability and myotonic discharges (Burge and Hanna, Curr Neurol Neurosci Rep 2012; 12:62-69).

Myotonia is a distinctive symptom of various genetic and acquired diseases which can be classified as myotonic disorders such as non-dystrophic myotonias and myotonic dystrophies.

The non-dystrophic myotonias (NDMs) are pure skeletal muscle diseases without the involvement of the heart or muscles in the digestive tract. Depending on the type and seriousness of the disorder, myotonia can affect anything from the legs, face, hands, hips, shoulders, feet, eyelids, to a person's ability to speak clearly. Emotional surprises, cold, potassium or exercise are potential triggers for myotonia.

In the more severe cases, NDMs can be chronically debilitating due to pain and muscle stiffness. A very few case of perinatal death has been reported as an unhappy complication of a severe myotonic condition called SNEL (Severe Neonatal Episodic Laryngospasms) (Gay et al., Am J Med Genet A 2008; 146:380-383; Lion-Francois et al., Neurology 2010; 75(7):641-645. Portaro et al., Pediatrics 2016; 137(4); Lehmann-Horn et al., Acta Myologica 2017; XXXVI:125-134). Very recently, myotonic mutations in the sodium channel has been pinpointed as a risk factor for SIDS (Sudden Infant Death Syndrome) (Mannikko et al., Lancet 2018; 391(10129):1483-1492).

The NDMs can be classified as ion channel disorders caused by conventional point mutations or deletions in the chloride or sodium channel genes with exclusive expression in skeletal muscle. The NDMs are known to be caused by gain-of-function mutations in SCN4A gene encoding the skeletal muscle $Na_V1.4$ sodium channel (paramyotonia congenita and sodium channel myotonia) or loss-of-function mutations in CLCN1 gene encoding the skeletal muscle ClC-1 chloride channel (myotonia congenita).

The reduced activity of mutated chloride channels or increased activity of mutated sodium channels determine a pathological sarcolemma hyperexcitability, with occurrence of high-frequency action potential discharges; the consequent difficulty in muscle relaxation is responsible for the characteristic stiffness of myotonic muscle.

The NDMs include chloride channelopathies, such as, for example, Thomsen's myotonia congenita and Becker myotonia congenita; and sodium channelopathies such as, for example, paramyotonia congenita with/without hyperkalemic periodic paralysis and sodium channel myotonias (SCMs), which include, for example, myotonia fluctuans, myotonia permanens and acetazolamide-responsive myotonia, K+ aggravated myotonia, and severe neonatal episodic laringospasm (SNEL). All forms of myotonia congenita are caused by mutations that result in loss of function of the chloride channel ClC-1, which is expressed exclusively in skeletal muscle membrane.

The following clinical description and potential therapeutic options for the above listed NDMs have been taken from Review Article Myotonic disorders of Ami Mankodi, published in Neurology India, July-September 2008, Vol. 56, Issue 3.

Thomsen's Myotonia Congenita

The name Thomsen's myotonia congenita is derived from the original description of the disease in the 1870s by the Danish physician in himself and his family members with autosomal dominant inheritance pattern. The symptoms begin during infancy or childhood. Patients report painless muscle stiffness on muscle activation after rest. Myotonia may decrease on repetitive muscle efforts, the so-called warm-up phenomenon. Emotional surprises, cold, or pregnancy may worsen myotonia. Physical examination may reveal athletic appearance with muscle hypertrophy in extremities and facial muscles in some patients. Patients demonstrate hand grip myotonia and eyelid myotonia. Patients may have trouble sitting up quickly after lying supine for several minutes reflecting myotonia in paraspinal and proximal muscles in the extremities. Muscle strength is normal. Prognosis is good in most patients. Patients with disabling myotonia may obtain benefit with mexiletine 150 mg by mouth twice a day with a gradual titration to maximum dose of 300 mg by mouth three times a day.

Becker's Myotonia Congenita

Becker's myotonia is an autosomal recessive chloride channel myotonia. The name is derived from the researcher who described this condition in the 1970s. Clinical presentation includes generalized myotonia and muscle hypertrophy similar to Thomsen's myotonia. However, there are important differences: onset is insidious and later during childhood; symptoms are often in the lower extremities at onset (the so-called ascending myotonia congenita); slowly progressive weakness in some patients; transient episodes of proximal muscle weakness lasting for seconds or minutes and may be triggered by asking the patient to arise quickly after several minutes of supine rest; and more pronounced hypertrophy of muscles in the lower extremities. Exposure to cold, prolonged muscular strain, pregnancy, menses, and emotional tension can exacerbate myotonia. Physical examination reveals athletic appearance with muscle hypertrophy, particularly involving muscles in the lower extremities and around shoulders. Some patients may show muscle atrophy in the forearms, hands and anterior neck. Myotonia is easily recognized in many muscle groups including masticatory muscles, tongue and neck muscles in addition to grip myotonia and eyelid lag. Most characteristic finding is marked difficulty in arising from the supine position and climbing stairs which gradually improves after several steps, secondary to warm-up phenomenon. This is thought to be due to a combination of myotonia and muscle weakness. Most patients notice muscle weakness upon activity after a period of rest. Some patients may have persistent lower extremity weakness, which can be disabling in the activities of daily living. Muscle stretch reflexes may be depressed in the lower extremities. Creatine Kinase (CK) levels may be increased. Repetitive nerve stimulation and short exercise test may show decline in the compound muscle action potential (CMAP) amplitude. Long exercise test may reveal a small decrement, which is not a feature in Thomsen's myotonia. Most patients enjoy good quality of life. Symptoms are only slowly progressive and may stabilize after a patient reaches the third decade. Treatment is directed towards activity modifications, avoidance of triggers for myotonia and weakness. In some patients with disabling myotonia pharmacological therapy including mexiletine, tocainide or acetazolamide is beneficial.

Paramyotonia Congenita (PMC)

Paramyotonia congenita refers to myotonia, which worsens with exercise, particularly in cold temperatures. Symptoms begin during infancy or childhood. Typical presentation includes prolonged eye closure after crying in infants or washing face in cold water and "frozen tongue" after eating ice cream. Some patients may report flaccid weakness after exercising in cold temperatures. Potassium ingestion, rest followed by exercise and prolonged fasting may also aggravate paramyotonia. Physical examination reveals prominent eyelid paramyotonia manifest as inability to open the eyes after repeated sustained eye closure or sustained lid retraction after a prolonged upward gaze. Placement of ice pack on eyelids may aggravate paramyotonia. Immersion of the hand in ice cold water for 10-15 min prior to hand grip exercise may provoke paramyotonia and subsequent weakness. Motor and sensory nerve conduction studies are normal. Repetitive nerve stimulation at 5 Hz may result in decrement in CMAP amplitudes. Similarly, short exercise test after cold exposure may also result in decrement response. The electromyography (EMG) reveals myotonia in many muscles. Fibrillation potentials and positive sharp waves may become evident after exposure to cold. Silent muscle contracture may occur with extreme cold exposure. Single-fiber EMG may show increase jitter and occasionally blocking. Muscle biopsy is not indicated for the diagnosis. In most patients, avoiding triggers such as exercise and cold exposure are sufficient to maintain good quality of life. Mexiletine can be used for disabling paramyotonia.

The Potassium-Sensitive Myotonias

There are three distinct sodium channel myotonic disorders, in which the myotonia is aggravated by potassium ingestion. Cold exposure generally does not worsen myotonia as it does in paramyotonia congenita. Weakness is not a prominent symptom.

Myotonia fluctuans is characterized by generalized myotonia triggered by potassium ingestion or by exercise. In contrast to paramyotonia, patients may have a warm-up effect after initial exercise, however, the myotonia becomes more pronounced after a second bout of exercise following a period of rest of about 20-40 min. Patients report fluctuation in the severity of myotonia with periods of no evident myotonia lasting for hours to days. Muscle bulk and strength are normal. The CK levels may be elevated by two to three-folds. The EMG may reveal myotonia and fibrillation potentials. Nerve conduction studies are normal. Muscle biopsy may reveal mild abnormalities such as increased internal nuclei, fiber size variability and sub-sarcolemma vacuoles. Most patients do not require medication. Simple avoidance of potassium-rich food items may be sufficient. Mexiletine can be helpful to relieve disabling myotonic stiffness.

Myotonia permanens is a rare and severe form of non-dystrophic myotonia. Clinical presentation includes onset before age 10 years, severe generalized myotonia, and muscle hypertrophy. Muscle weakness is not prominent. Severe myotonia involving intercostal muscles may result in respiratory compromise with hypoxemia and acidosis. Potassium ingestion and exercise are the usual triggers for myotonia. The EMG reveals generalized myotonia with normal motor unit potentials. Mexiletine may provide partial relief from myotonic stiffness. Acetazolamide may help relieve exercise-induced muscle stiffness or cramps. Acetazolamide-responsive myotonia is characterized by generalized myotonia worsened by potassium ingestion, cold and fasting, and excellent recovery with acetazolamide. Patients present during childhood with progressive generalized myotonia, which is easily evident on clinical examination and by EMG. Eyelid paramyotonia may be seen in some patients. Myotonic stiffness can be painful. Exercise generally has no significant effect on myotonia. Treatment includes acetazolamide with starting dose 125 mg daily with gradual titration up to 250 mg three times a day if required. Side effects include kidney stone formation, paresthesia, nausea, confusion, mood irritability, depression, rash and liver function abnormalities. Regular monitoring of complete blood count and liver functions is recommended. Mexiletine can also relieve myotonia.

The NDMs are distinct from myotonic dystrophies because of the absence of progressive weakness and systemic features.

Myotonic dystrophies (DMs) are diseases characterized by progressive myopathy, myotonia, and multiorgan involvement.

The presence of myotonia is not the most disabling aspect of DMs, but it is the recognized hallmark of the condition, and the aspect of the disease that distinguishes it from other forms of muscular dystrophy.

To date, two distinct forms caused by similar mutations have been identified: myotonic dystrophy type 1 (DM1) and myotonic dystrophy type 2 (DM2).

In particular, DM1 and DM2 are inherited human diseases due to the expansion of nucleotide repeats in chromosome 19 and 3, respectively (Meola, Acta Myol. 2013; 32(3):154-165). Such alteration leads to accumulation of toxic RNA in the nucleus, which affects normal protein processing in many cell types. Thus, DM1 and DM2 are multi systemic diseases affecting for instance CNS, heart, and skeletal muscle. In the later, the ClC-1 channel is a target of this toxic process. The reduction of ClC-1 protein and alteration of its splicing is the main responsible for myotonia in DM1 and DM2 patients (Charlet-B et al., Mol Cell. 2002; 10(1):45-53; Mankodi et al., Mol Cell. 2002; 10(1):35-44; and Chen et al., J Mol Biol. 2007; 368(1):8-17).

Currently, myotonia medications are aimed to reducing pathological sarcolemma hyperexcitability. Those medication include mexiletine (Logigian et al., Neurology 2010; 74(18):1441-1448).

SUMMARY OF THE INVENTION

Searching for anti-myotonic drugs operating through to the reduction of pathological sarcolemma hyperexcitability, the present inventors have found that safinamide is able to restore sarcolemma excitability in isolated myotonic muscle fibers and to alleviate myotonic symptoms in vivo in a pharmacologically-induced rat model of myotonia. Therefore, the present invention relies of this finding and refers to safinamide as an anti-myotonic drug for treating patients with myotonic disorders in need thereof.

The present invention also refers to pharmaceutical compositions comprising safinamide or a pharmaceutically acceptable salt thereof in combination with suitable excipients, vehicles or carriers, for use in myotonic disorders.

DETAILED DESCRIPTION OF THE INVENTION

Figure 1:
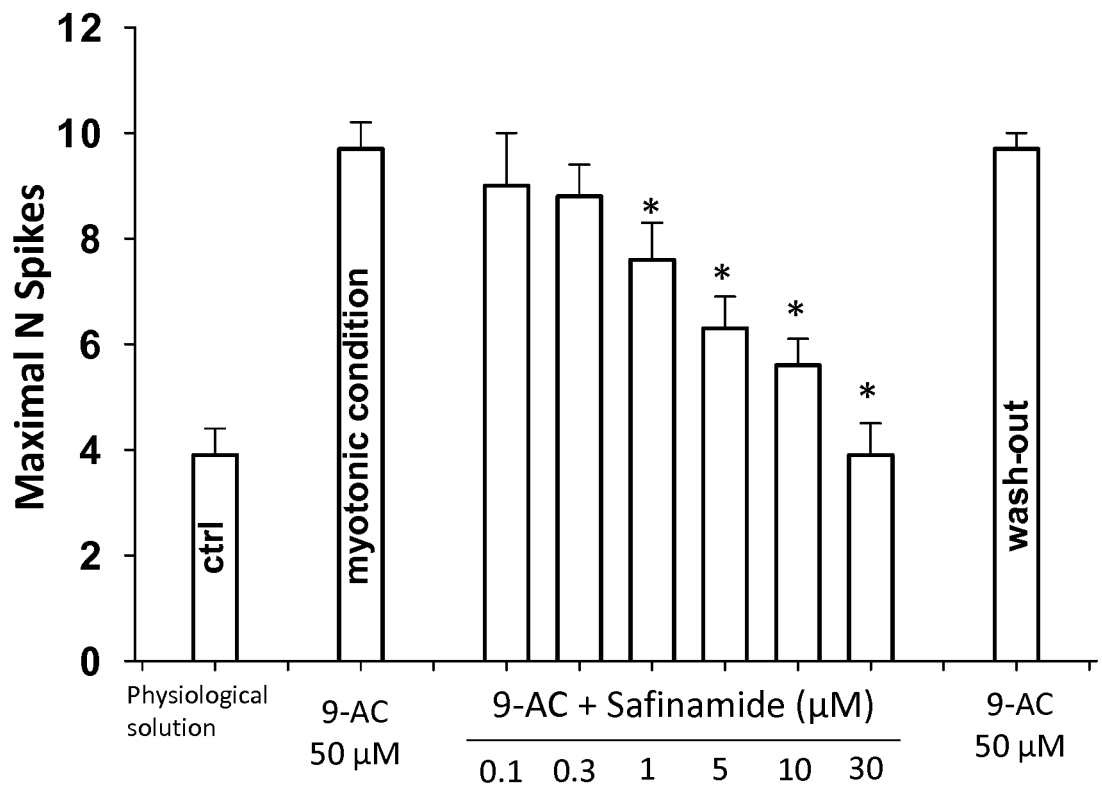
FIG. 1 shows the in vitro antimyotonic effect of safinamide on rat skeletal muscle fiber excitability in a myotonia-like condition induced by 9-anthracene carboxylic acid (9-AC). Skeletal muscle fiber excitability (maximum number of spikes, N spikes) was measured before (control, ctrl), after 50 μM 9-AC alone and, after concomitant application of safinamide at six different concentrations (0.1 to 30 μM). The antimyotonic effect was reversible upon safinamide wash-out (50 μM 9-AC, rightmost column). Results were expressed as Mean±S.E.M; P<0.05 vs 9-AC alone, Bonferroni's t test.

Accordingly, the present invention relates to safinamide or a pharmaceutically acceptable salt thereof for use in the treatment of a condition caused by pathological sarcolemma hyperexcitability, and/or of any other condition in which the restoration of normal sarcolemma excitability may produce a therapeutic benefit or improvement, wherein such a condition is a myotonic disorder.

As a matter of fact, up to 30% of patients with myotonic disorders find mexiletine (the reference drug in myotonic disorders) ineffective (Desaphy et al., 2013; Suetterlin et al., JAMA Neurol. 2015 December; 72(12): 1531-3; Portaro et al., 2016). For the purpose of the present invention, myotonic disorders where mexiletine is ineffective have been defined mexiletine-resistant and a further embodiment of the present invention relates to the use of safinamide in the treatment of mexiletine-resistant myotonic disorders.

Furthermore, the present invention relates to safinamide or a pharmaceutically acceptable salt thereof for use in the treatment of a myotonic disorder, wherein the myotonic disorder is, preferably, a non-dystrophic myotonia (NDM).

Even more preferably, NDM patients to whom safinamide may be beneficial carry a missense mutation in the SCN4A gene. In fact, without being bound to any particular theory and as better detailed in the experimental part, it has been found that safinamide potency, measured as $IC_{50}$ values at resting membrane potential and after repetitive depolarizing pulses, doesn't decrease, compared to the wild type, in cells transfected with the missense mutations in the $hNa_v1.4$ channel (Desaphy et al., 2001, 2003 and 2016). A compound able to block sodium channels in a use and frequency-dependent manner is expected to decrease the abnormal firing but to leave unaffected the normal muscle fiber activity.

On the contrary, notably, mexiletine potency significantly decreases in hNav1.4 point mutations transfected cells.

In a further embodiment, the present invention relates to safinamide or a pharmaceutically acceptable salt thereof for use in the treatment of a NDM, wherein such a NDM is, preferably, a myotonia congenita such as, for example, Thomsen's myotonia congenita or Becker myotonia congenita, paramyotonia congenita or a sodium or chloride channel myotonia; more preferably, said sodium channel myotonia is a $hNa_v1.4$ channelopathy and the patient in need thereof is a carrier of mutation in the SCN4A gene, encoding the $hNa_v1.4$ channel. In a further embodiment, the present invention relates to safinamide or a pharmaceutically acceptable salt thereof for use in the treatment of a myotonia congenita, wherein such a myotonia congenita is Thomsen's myotonia congenita or Becker myotonia congenita.

In a preferred embodiment, the present invention relates to safinamide or a pharmaceutically acceptable salt thereof for use in the treatment of paramyotonia congenita.

Further in addition, the present invention relates to safinamide or a pharmaceutically acceptable salt thereof for use in the treatment of a sodium channel myotonia, wherein such a sodium channel myotonia is myotonia fluctuans, myotonia permanens or acetazolamide-responsive myotonia.

Furthermore, the present invention relates to safinamide or a pharmaceutically acceptable salt thereof for use in the treatment of a myotonic disorder, wherein such a myotonic disorder is preferably a DM.

Even further, the present invention relates to safinamide or a pharmaceutically acceptable salt thereof for use in the treatment of a DM, wherein such a DM is preferably selected from DM1 and DM2.

In a preferred aspect, the present invention relates to safinamide or a pharmaceutically acceptable salt thereof for use in the treatment of a myotonia congenita.

In another aspect, the present invention relates to safinamide or a pharmaceutically acceptable salt thereof for use in alleviating one or more of myotonic symptoms associated with a condition as defined above, wherein myotonic symptoms includes skeletal muscle stiffness, spasms, and pain. According to the present invention, safinamide is (2S)-2-[[4-[(3-fluorophenyl)methoxy]phenyl]methylamino]propanamide, of formula:

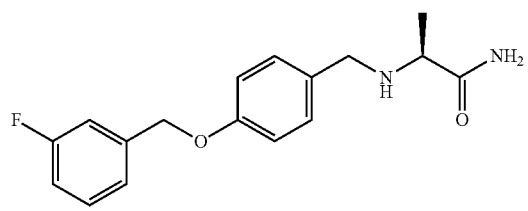 [SMILES: C[C@H](NCc1ccc(OCc2cccc(F)c2)cc1)C(N)=O]

Safinamide is preferably in the form of a pharmaceutically acceptable salt. Pharmaceutically acceptable salts of safinamide include addition salts with inorganic acids, for example nitric, hydrochloric, sulphuric, perchloric and phosphoric acid or with organic acids, for example acetic, propionic, glycolic, lactic, oxalic, malonic, malic, tartaric, citric, benzoic, cinnamic, mandelic, methanesulphonic and salicylic acid; safinamide methanesulfonate (mesylate) being the preferred salt.

As used herein, the articles "a" and "an" refer to one or to more than one (e.g., to at least one) of the grammatical object of the article.

As used herein, the term "disease", "disorder", or "condition" is used interchangeably.

As used herein, the term "treating" or "treatment", refers to obtaining the desired pharmacological effect including reversing, alleviating, inhibiting the progress of, or preventing the disorder or condition to which such term applies, or one or more symptoms of such disorder or condition.

Safinamide or a pharmaceutically acceptable salt thereof is typically included in a pharmaceutical composition.

A pharmaceutical composition for the treatment of myotonic disorders as defined above and according to the present invention, comprises safinamide or a pharmaceutically acceptable salt thereof in an effective amount, sufficient to provide either the desired therapeutic effect or the relief of symptoms of myotonic disorders. The pharmaceutical composition comprises pharmaceutically acceptable carrier or excipient.

A pharmaceutical composition according to the present invention may be administered to a subject/patient by any convenient route of administration, whether systemically/peripherally or topically (i.e., at the site of desired action).

A pharmaceutical composition according to the present invention can be formulated for oral administration, topical administration, transdermal administration, parenteral administration and combinations thereof. Preferred compositions are for oral or parenteral administration. Suitable forms for oral administration include tablets, compressed or coated pills, sachets, troches, granulates, hard or soft gelatin capsules, sublingual tablets, syrups, solutions, and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

The pharmaceutical compositions according to the present invention can be prepared by processes, which are known per se and familiar to the person skilled in the art.

The dosage regimen for safinamide or a pharmaceutically acceptable salts thereof and/or pharmaceutical compositions containing the same, is based on a variety of factors, including the type, age, weight, sex and medical condition of the subject, the severity of the condition and/or myotonic symptoms associated with said condition, and the route of administration.

Thus the dosage regimen may vary widely. Dosage levels of the order from about 5 to about 500 mg per day (administered in single or divided doses) of safinamide or a pharmaceutically acceptable salts thereof are useful in the treatment of the above-indicated conditions. In one embodiment, the total daily dose is typically from about 10 to about 250 mg. In another embodiment, the total daily dose is typically from about 50 to about 100 mg.

Safinamide methanesulfonate film-coated oral tablets, at a dosage of 50 and 100 mg, are currently on the market under the tradename Xadago®.

According to the present invention, the antimyotonic activity of safinamide has been assessed by using experimental protocols that mimic myotonic conditions both in vitro (sarcolemma hyperexcitability in myotonic skeletal muscle fibers) and in vivo (pharmacologically-induced rat model of myotonia congenita mimicking the human pathological condition in which a genetic loss of chloride conductance causes impaired muscle relaxation and muscle stiffness; Desaphy et al., Neuropharmacology 2013, 65: 21-7; and Desaphy et al., Exp Neurol 2014; 255: 96-102).

Figure 2:
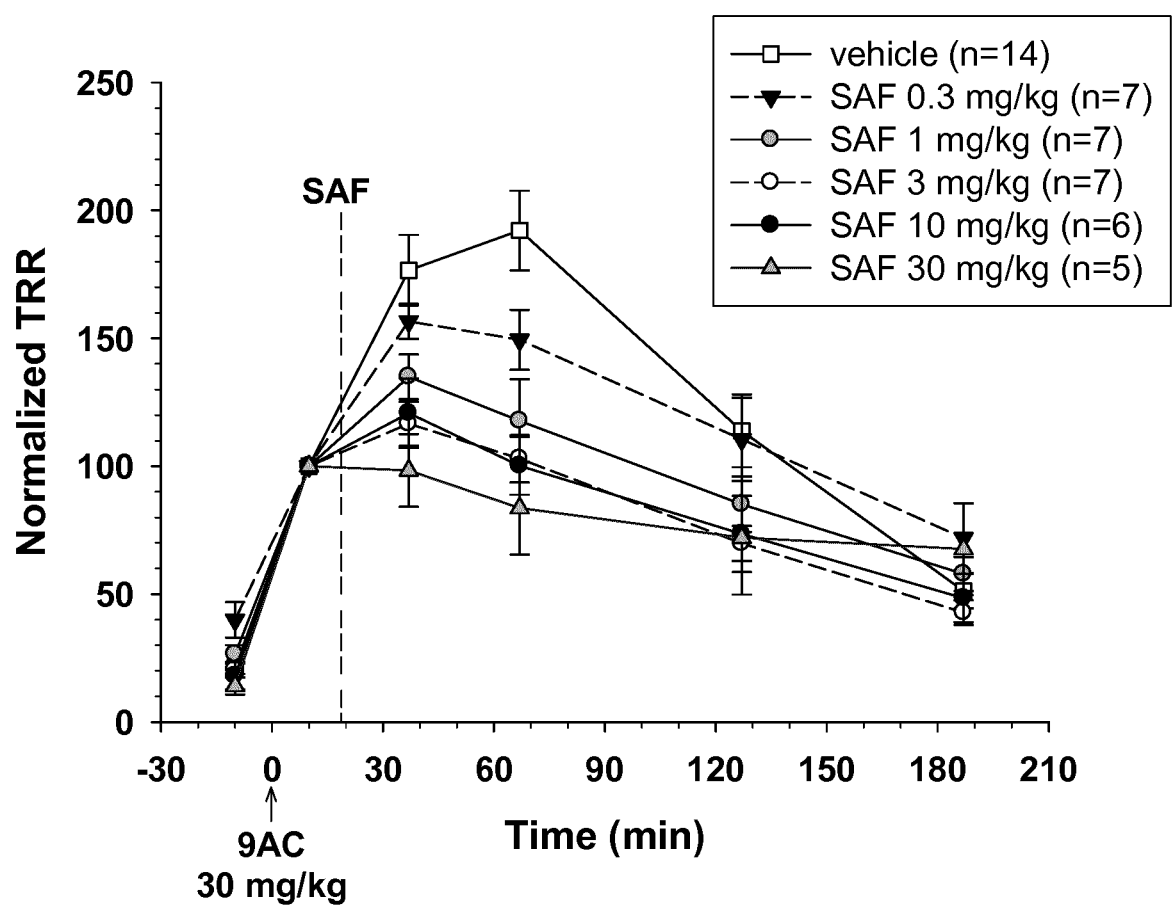
FIG. 2 shows the in vivo antimyotonic dose-response effect of safinamide in a pharmacologically-induced rat model of myotonia congenita. Safinamide at 0.3, 1, 3, 10 and 30 mg/kg (respectively: black triangle, gray circle, empty circle, black circle, gray triangle; vehicle alone: empty square) given orally was able to counteract the 9-anthracene carboxylic acid (9-AC, 30 mg/kg)-induced time reflex righting (TRR) prolongation as sign of myotonia in the rat. Results were expressed as Mean±S.E.M, n=5-7 rats; P<0.05 vs vehicle, Bonferroni's t test.

The following Examples and their accompanying FIGS. 1 and 2 illustrate the invention without limiting its scope.

EXPERIMENTAL PART

Example 1. In Vitro Antimyotonic Activity of Safinamide in Rat Skeletal Muscle Fibers The antimyotonic activity of safinamide was assessed by recording the sarcolemma excitability in single myofibers of isolated Extensor Digitorum Longus (EDL) muscles using two-microelectrode current-clamp technique. The in-vitro model of myotonia congenita was obtained by incubating rat EDL muscles with 9-anthracene carboxylic acid (9-AC) (Conte Camerino et al., Muscle Nerve. 1989; 12(11):898-904. Altamura et al., Br J Pharmacol. 2018; 175(10):1770-1780). The increase of sarcolemma excitability caused by 9-AC through the blockade of skeletal muscle ClC-1 chloride channels mimicked the abnormal action potential firing observed in patients affected by myotonia congenita.

EDL muscles were dissected out from male Wistar rats under deep anaesthesia (80 mg/kg ip ketamine and 10 mg/kg ip xylazine). Muscles were placed in a 25 ml muscle bath maintained at 30° C. and perfused with saline (gassed with 95% $O_2$ and 5% $CO_2$; pH=7.2-7.3). By means of standard two-intracellular-microelectrode technique, the resting membrane potential and excitability characteristics (number of spikes) of muscle fibres were measured in current clamp mode. The excitability characteristics of the sampled fibres were determined by recording the intracellular membrane potential response to a square-wave constant (100 ms) current pulse. In each fibre, the membrane potential was set by a steady holding current to −80 mV before passing the depolarizing pulses. By increasing the amplitude of the pulse we were able to elicit the first single action potential and by further increasing current intensity in the same fibre, the maximum number of elicitable spikes (N spikes) was measured (Pierno et al., Br J Pharmacol. 2006; 149(7):909-19).

Unwarranted muscle contractions were hampered with dantrolene sodium (2 mg/l). Cell excitability parameters (N spikes) was measured before (control) and after 50 µM 9-AC alone and concomitant application of safinamide at six different concentrations (0.1 to 30 µM). In these experimental conditions, safinamide methanesulfonate was used and dissolved as stock solution (10 mM) in distilled water, then it was diluted to the final concentrations in the muscle bath solution. One animal was used to test two concentrations of safinamide: one concentration in each EDL muscle.

As shown in FIG. 1, 9-AC induced a myotonia-like condition by increasing N spikes by 60%. Safinamide at 1, 5, 10, and 30 µM significantly reduced N spikes by 22±6%, 35±5%, 42±5%, and 60±6%, respectively (P<0.05 vs 9-AC alone, Bonferroni's t-test) thus restoring the sarcolemma excitability. The $IC_{50}$ (the concentration able to reduce by 50% the 9-AC effect) and calculated from the fit of the concentration-response curve) was 13.4±2.4 µM (±SE of the fit). The antimyotonic effect was reversible upon safinamide wash-out (9-AC, 50 µM).

Of note, in the same test, mexiletine $IC_{50}$ was more than threefold higher, indicating a lower potency.

Example 2. Study of the In-Vivo Antimyotonic Activity of Safinamide in a Rat Model of Myotonia Congenita Myotonia was induced in rats by intraperitoneal injection of 9-AC, which is a known blocker of skeletal muscle ClC-1 chloride channels (Conte Camerino et al., Muscle Nerve. 1989; 12(11):898-904. Altamura et al., Br J Pharmacol. 2018; 175(10):1770-1780).

Male Wistar rats (250-300 g) were used. Experiments were performed in accordance with the Guide for the Care and Use of Laboratory Animals and with Italian Health Department approval n. 194/2018-PR. Experimenters were blinded to the treatments.

In this animal model, 9-AC mimics in vivo myotonia congenita, a human disease due to loss-of-function mutations in CLCN1 gene encoding ClC-1 channels. After 9-AC injection, the rats showed evident muscle stiffness, especially in hind limbs, and difficulties to move. Nevertheless, the animals remained fully conscious and alert. Breathing was normal. When hearing an unexpected noise, the animals reacted by a jump on site but had great difficulties to move away due to muscle stiffness. Myotonia was evaluated by measuring the time of righting reflex (TRR, the time needed for the rat placed in supine position to turn back on its four paws). In rats, before 9-AC injections the TRR was less than 0.5 s. The TRR was dramatically prolonged to about 2 s, 10 min after 9-AC, and increased further to about 4 s, 30 min after 9-AC. Then the TRR decreased gradually over time, being close to 1 s, 3 h after 9-AC. An anti-myotonic drug is expected to counteract the 9-AC-induced TRR prolongation.

The TRR was evaluated about 10 minutes before 9-AC (Time 0) and 10, 37, 67, 127, and 187 min after 9-AC (30 mg/kg i.p.). The TRR measured at each time point was the mean of 7 measurements spaced by 1 min (to limit warm-up effect). Safinamide methanesulfonate (10 and 30 mg/kg as free base) or vehicle were administrated by oral gavage to the rats 17 min after 9-AC injection. 9-AC and safinamide methanesulfonate were dissolved in bicarbonate and 0.9% NaCl solution, respectively. To allow comparison between rats, the TRR measured at each time point was normalized as a function of TRR measured 10 min after 9AC injection in the same rat. Then average data were calculated for each dosage as the mean±S.E.M. Statistical analysis was performed using one-way analysis of variance (ANOVA) followed by ad-hoc Bonferroni's t test. P value<0.05 was considered statistically significant.

As shown in FIG. 2, in vehicle-treated rats significant increases of the TRR were observed at 37, 67 and 127 min after 9-AC injection. At the peak effect (37 and 67 min), the concomitant treatment with safinamide dose-dependently and significantly counteracted the 9-AC-induced TRR prolongation and the effect lasted up 120 min demonstrating that in vivo safinamide was endowed with antimyotonic activity in a rat model of myotonia congenita.

In this in vivo model the dose-response curve of safinamide methanesulfonate at increasing doses (0.3, 1, 3, 10 and 30 mg/kg as free base) was also studied. To allow comparison between rats, the TRR measured at each time point was normalized as a function of TRR measured 10 min after 9AC injection in the same rat. Then average data were calculated for each drug/dosage as the mean±S.E.M. Statistical analysis will be performed using one-way analysis of variance (ANOVA) followed by ad-hoc Bonferroni's t test. P value<0.05 was considered statistically significant.

The results are shown in FIG. 2, which shows that in vehicle-treated rats significant increases of the TRR were observed at 37, 67 and 127 min after 9-AC injection. The treatment with safinamide dose-dependently and significantly counteracted the 9-AC-induced TRR prolongation. In fact, oral safinamide was able to counteract the 9-anthracene carboxylic acid (9-AC)-induced time reflex righting (TRR) prolongation as sign of myotonia in the rat.

In particular, at 37 min, reduction of TRR was significant with 3, 10 and 30 mg/kg safinamide. At 67 min (9-AC peak effect), TRR inhibition was significant also with the lower dose of 1 mg/kg safinamide. At 127 min, only 10 and 30 mg/kg produced significant inhibition. The analysis of dose-response curve at 67 min revealed an ED50 (effective dose in inhibiting by 50% TRR prolongation) of 1.2 mg/kg and maximal effect of 66% obtained with the dose of 10-30 mg/kg demonstrating that in vivo safinamide was endowed with significant antimyotonic activity in a rat model of myotonia congenita.

Of note, in the same test, the reference drug for myotonias, mexiletine, was about 6-fold less potent.

Example 3. In Vitro Effect of Safinamide on Selected Human $Na_v1.4$ Myotonia Mutations in Transfected Cell Lines Over forty different mutations of $hNa_v1.4$ have been linked to several phenotypically different human autosomal dominant inherited skeletal muscle disorders (Cummins & Bendahhou, 2009; Jurkat-Rott et al. 2010).

The Nav1.4 channel is mainly expressed in skeletal muscle and it is composed of a 260 kDa α-subunit that is associated with a smaller β-subunit in the muscle. The α-subunit consists of four homologous domains (I-IV), and each domain has six trans-membrane segments (S1-S6) (Noda et al., 1984). Nav1.4 channel mutations leading to periodic paralysis or non-dystrophic myotonia have been found throughout each domain and segment of this channel and may underlie the muscle hyperexcitability or inexcitability by changing channel kinetics or function, thereby producing changes in the micro- or macroscopic biophysical properties of the channel. Several Nav1.4 channel mutations associated with myotonia have been described to alter channel function by slowing fast inactivation, increasing the rate of recovery from fast inactivation, slowing deactivation or shifting the voltage dependence of activation to more negative potentials (Cummins & Bendahhou, 2009).

The effect of safinamide was evaluated on some hNav1.4 point mutations located in the inactivation site.

p.P1158L: this mutation was found in an Algerian young girl, and is associated to severe myotonia permanens (Desaphy et al., 2016).

p.V1293I: the V1293I mutation is associated to various phenotypes, from sodium channel myotonia to paramyotonia congenita+hyperkalemic periodic paralysis (Koch et al., 1995).

p.F1298C: this mutation was found in a 35-year-old female, presenting at the age of 32 with stiffness in facial, upper and lower limb muscles, mainly after contraction (Farinato et al., 2019). Symptoms worsened with cold and myotonia was reported as painful. The patient noticed a mild improvement of myotonia with exercise.

p.I1310N: this mutation has been found in 5 related of a French kindred, and is associated to sodium channel myotonia (Farinato et al., 2019).

Human skeletal muscle subtype of voltage-gated sodium channels (hNav1.4), either wild-type or myotonic mutants, were transiently transfected in HEK293T cells with the calcium-phosphate co-precipitation method. Whole-cell sodium currents (INa) were recorded at room temperature (20-22° C.) using Axon conventional patch-clamp hardware (Molecular Devices, USA). Voltage clamp protocols and data acquisition were performed with pCLAMP software (Axon Instruments). Bath solution contained (mM) 150 NaCl, 4 KCl, 2 $CaCl_2$, 1 $MgCl_2$, 5 Na-HEPES, and 5 glucose (pH 7.4). The pipette solution contained (in mM) 120 CsF, 10 CsCl, 10 NaCl, 5 EGTA, and 5 Cs-HEPES (pH 7.2). Patch pipettes made with Corning 7052 glass (King glass, USA) had resistance ranging from 1 to 3 MΩ. Capacitance currents were partially compensated using the amplifier circuit. Only those data obtained from cells exhibiting series resistance errors <5 mV were considered for analysis. After rupturing the patch membrane, a 25-ms-long test pulse to −20 mV from a holding potential (hp) of −120 mV was applied to the cell at a low frequency until stabilization of INa amplitude and kinetics was achieved (typically 5 minutes). Safinamide was solubilized at the final concentration in bath solution supplemented with 0.2% DMSO. The patched cell was exposed to a continuous stream of control or drug-supplemented bath solution. A maximum of two drug concentrations were tested on each cell, to minimize the possible bias due to sodium current rundown. Because of the known spontaneous shift of voltage dependence during whole-cell experiments, much care was taken to perform the various protocols respecting a constant sequence to allow comparison between the cells.

Inhibition of hNav1.4 channels by safinamide was evaluated by measuring the reduction of INa elicited from a holding potential (HP) of −120 to −30 mV at frequency stimulations of 0.1 and 10 Hz. The concentration-response curves of safinamide were produced by obtaining the peak current amplitude measured in the presence of drug (IDRUG), normalized to the peak current amplitude measured in the same cell before drug application (ICTRL), as a function of drug concentration [(DRUG)]. The concentration-response curves were fitted with a first-order binding function:

$$IDRUG/ICTRL = 1/\{1+([DRUG]/IC_{50})^{nH}\}$$

where $IC_{50}$ is the half-maximum inhibitory concentration and nH is the slope factor. The $IC_{50}$ values were determined at resting membrane potential (tonic block: −120 mV at 0.1 Hz) and after repetitive depolarizing pulses to −20 mV at 10 Hz (use and frequency-dependent block). A compound able to block sodium channels in a use and frequency-dependent manner is expected to decrease the abnormal firing but leaving unaffected the normal muscle fiber activity.

Table 1 shows the in vitro effects of safinamide on human $Na_v1.4$ sodium channel myotonia mutants in transfected cell lines. The results were expressed as $IC_{50}$ values±Standard Error of the fit (SE).

TABLE 1

Effect of safinamide on human $Na_v1.4$ sodium channel myotonia mutants in a transfected cell line.

| $hNa_v1.4$ channel mutation | $IC_{50} \pm SE$ (μM) Tonic block at 0.1 Hz | $IC_{50} \pm SE$ (μM) Use and frequency-dependent block at 10 Hz |
|---|---|---|
| Wild Type $hNa_v1.4$ | 160 ± 18 | 33 ± 4 |
| P1158L | 148 ± 13 | 34 ± 3 |
| V1293I | 171 ± 19 | 47 ± 5 |
| F1298C | 173 ± 12 | 83 ± 2 |
| I1310N | 170 ± 26 | 46 ± 7 |

The results shown in Table 1 demonstrate that the selected mutations had no significant effect on safinamide potency ($IC_{50}$) at both frequencies (0.1 and 10 Hz), as the $IC_{50}$ values were of the same magnitude order to wild type. Carriers of the mutations in the hNav1.4 channel may obtain more benefits with safinamide than with the drugs currently used.

These results paves the way for mutation-driven therapy of myotonic disorders.

The invention claimed is:

1. Method of treating myotonic disorders in patients in need thereof, said method comprising
administering to said patients a pharmaceutically effective amount of safinamide or a pharmaceutically acceptable salt thereof and treating said patients of said myotonic disorders, wherein the myotonic disorder is a non-dystrophic myotonia.

2. The method according to claim 1, wherein said myotonic disorder is mexiletine-resistant.

3. The method according to claim 1, wherein the non-dystrophic myotonia is a myotonia congenita.

4. The method according to claim 1, wherein the non-dystrophic myotonia is a sodium or chloride channel myotonia.

5. The method according to claim 4, wherein said sodium channel is hNav1.4.

6. The method according to claim 3, wherein the myotonia congenita is Thomsen's myotonia congenita or Becker myotonia congenita.

7. The method according to claim 4, wherein the sodium channel myotonia is paramyotonia congenita.

8. The method according to claim 1, further comprising alleviating one or more of myotonic symptoms associated with myotonic disorders.

9. The method according to claim 8, wherein the myotonic symptoms are selected in the group comprising: skeletal muscle stiffness, spasm and pain.

10. The method according to claim 1, wherein safinamide is in the form of methanesulfonate (mesylate) salt thereof.

11. The method according to claim 1, wherein safinamide or a pharmaceutically acceptable salt thereof is comprised in a pharmaceutical composition in combination with a pharmaceutical carrier, vehicle and/or excipient.

12. Method of treating myotonic disorders in patients in need thereof, said method comprising
administering to said patients a pharmaceutically acceptable amount of pharmaceutical composition comprising safinamide or a pharmaceutically acceptable salt thereof in combination with a pharmaceutical carrier and/or excipient, and treating said patients of said myotonic disorders, wherein said myotonic disorder is a non-dystrophic myotonia.

13. The method according to claim 12, wherein said pharmaceutical composition is administered orally or parenterally.

14. The method according to claim 12, wherein said myotonic disorders are mexiletine resistant myotonic disorders.

15. Method of treating myotonic disorders or relieving symptoms thereof in patients in need thereof, said method comprising administering to said patients a pharmaceutically effective amount of a medicament comprising safinamide and treating said patients of said myotonic disorders or relieving symptoms thereof, wherein said myotonic disorder is a non-dystrophic myotonia.

* * * * *